(12) United States Patent
Lading et al.

(10) Patent No.: US 10,959,622 B2
(45) Date of Patent: Mar. 30, 2021

(54) METHOD FOR DETERMINING PULSE WAVE VELOCITY IN AN ARTERY

(71) Applicant: PHILIPS HEALTHCARE INFORMATICS, INC., Cambridge, MA (US)

(72) Inventors: Lars Lading, Roskilde (DK); David Boettcher Baek, San Diego, CA (US)

(73) Assignee: Koninklijke Philips N.V., Eindhoven (NL)

( * ) Notice: Subject to any disclaimer, the term of this patent is extended or adjusted under 35 U.S.C. 154(b) by 337 days.

(21) Appl. No.: 14/625,110

(22) Filed: Feb. 18, 2015

(65) Prior Publication Data
US 2015/0238095 A1 Aug. 27, 2015

Related U.S. Application Data

(60) Provisional application No. 61/943,777, filed on Feb. 24, 2014.

(51) Int. Cl.
*A61B 5/02* (2006.01)
*A61B 5/0285* (2006.01)
(Continued)

(52) U.S. Cl.
CPC .......... *A61B 5/02007* (2013.01); *A61B 5/024* (2013.01); *A61B 5/0245* (2013.01);
(Continued)

(58) Field of Classification Search
CPC .. A61B 5/02108; A61B 5/02133; A61B 5/022
See application file for complete search history.

(56) References Cited

U.S. PATENT DOCUMENTS

| 4,660,564 A * | 4/1987 | Benthin | A61B 5/02007 600/449 |
| 5,241,963 A * | 9/1993 | Shankar | A61B 5/02007 600/481 |

(Continued)

FOREIGN PATENT DOCUMENTS

| CN | 101288586 A | 10/2008 |
| CN | 100560019 C | 11/2009 |

(Continued)

OTHER PUBLICATIONS

Hui. "Using Excel statistical functions for trend analysis: Are You Trendy? Part 2" (Jun. 30, 2011) Accessed May 7, 2020. Retrieved from https://chandoo.org/wp/trendlines-and-forecasting-in-excel-part-2/ (Year: 2011).*

(Continued)

*Primary Examiner* — Bill Thomson
*Assistant Examiner* — Helene Bor (57) ABSTRACT

Methods, devices, and systems for determining an estimated pulse wave velocity of an artery of a subject. Embodiment methods may include applying a series of counter pressures, measuring a first parameter related to pulse wave velocity, estimating a second parameter in a model, and determining the estimated pulse wave velocity. The counter pressures may be applied at a set location on the subject over the artery with a pressure device. Each of the counter pressures may be different from one another, applied at the set location, and between zero and a diastolic pressure of the subject. The first parameter may be measured when each of the series of counter pressures is applied. The model may establish a relationship of the first parameter measured to each of the series of counter pressures. The estimated pulse wave velocity may be determined based on the second parameter estimated in the model.

52 Claims, 4 Drawing Sheets

(51) Int. Cl.
  *A61B 5/053* (2006.01)
  *A61B 5/024* (2006.01)
  *A61B 5/021* (2006.01)
  *A61B 5/0245* (2006.01)
  *A61B 5/055* (2006.01)
  *A61B 5/00* (2006.01)
  *A61B 8/02* (2006.01)

(52) U.S. Cl.
  CPC ........ *A61B 5/0285* (2013.01); *A61B 5/02108* (2013.01); *A61B 5/02125* (2013.01); *A61B 5/02422* (2013.01); *A61B 5/053* (2013.01); *A61B 5/055* (2013.01); *A61B 5/7275* (2013.01); *A61B 8/02* (2013.01)

(56) References Cited

U.S. PATENT DOCUMENTS

| | | | |
|---|---|---|---|
| 6,141,578 A * | 10/2000 | Hardy | A61B 5/0285 600/410 |
| 6,331,162 B1 | 12/2001 | Mitchell | |
| 6,358,213 B1 * | 3/2002 | Friedman | A61B 5/022 600/493 |
| 6,983,662 B2 | 1/2006 | McLaughlin et al. | |
| 7,674,231 B2 | 3/2010 | McCombie et al. | |
| 8,313,439 B2 | 11/2012 | McCombie et al. | |
| 8,419,649 B2 | 4/2013 | Banet et al. | |
| 8,672,854 B2 | 3/2014 | McCombie et al. | |
| 9,706,931 B2 * | 7/2017 | Fuke | A61B 5/02108 |
| 2003/0163051 A1 * | 8/2003 | Eckerle | A61B 5/6822 600/485 |
| 2004/0044288 A1 * | 3/2004 | Gorenberg | A61B 5/02141 600/481 |
| 2005/0154299 A1 | 7/2005 | Hoctor et al. | |
| 2006/0149522 A1 * | 7/2006 | Tang | G06F 19/321 703/11 |
| 2006/0211942 A1 * | 9/2006 | Hoctor | A61B 8/4236 600/438 |
| 2006/0247538 A1 | 11/2006 | Davis | |
| 2008/0262362 A1 * | 10/2008 | Kolluri | A61B 5/02125 600/490 |
| 2008/0275351 A1 * | 11/2008 | Kirchberg | A61B 5/0285 600/500 |
| 2010/0152547 A1 * | 6/2010 | Sterling | A61B 5/029 600/301 |
| 2013/0079648 A1 | 3/2013 | Fukuzawa et al. | |
| 2013/0184595 A1 | 7/2013 | Mukkamala et al. | |
| 2013/0331678 A1 | 12/2013 | Lading et al. | |
| 2014/0066788 A1 * | 3/2014 | Mukkamala | A61B 5/02125 600/485 |

FOREIGN PATENT DOCUMENTS

| | | |
|---|---|---|
| EP | 2554111 A1 | 2/2013 |
| JP | H0260628 A | 3/1990 |
| JP | H0866377 A | 3/1996 |
| JP | 2003250772 A | 9/2003 |
| JP | 2003529434 A | 10/2003 |
| JP | 2006102181 A | 4/2006 |
| JP | 2007044364 A | 2/2007 |
| WO | 2007023426 A2 | 3/2007 |
| WO | 2012021765 A2 | 2/2012 |
| WO | 2012110042 A1 | 8/2012 |
| WO | 2013110929 A1 | 8/2013 |

OTHER PUBLICATIONS

Blood Pressure Cuff Selection and Sizing. Accessed May 7, 2020. Retrieved from <http://healthcaresciencesocw.wayne.edu/vs/6_6.htm> (Year: 2005).*

Caro C.G., et al., The Mechanics of the Circulation (Cambridge Univ. Press, Cambridge 2012), pp. 269-299.

Dogui A., et al., "Measurement of Aortic Arch Pulse Wave Velocity in Cardiovascular MR: Comparison of Transit Time Estimators and Description of a New Approach", Journal of Magnetic Resonance Imaging, vol. 33 (6), 2011, pp. 1321-1329.

Frans N., et al., "Pulse Wave Propagation in the Arterial Tree," Annual Review of Fluid Mechanics, 2011, pp. 467-499.

Fung Y.C., "Biomechanics: Mechanical Properties of Living Tissue," 2nd Ed. Springer, 1993, pp. 349-351.

Khamdaeng T., et al., "Arterial Stiffness Identification of the Human Carotid Artery Using the Stress-Strain Relationship in Vivo," Ultrasonics, vol. 52 (3), 2012, pp. 402-411.

Melis M D., et al., "A Noncontact Approach for Evaluation of Large Artery Stiffness: A Preliminary Study," American Journal of Hypertension, vol. 21, No. 12, 2008, pp. 1280-1283.

Westerhof N., et al., "Snapshots of Hemodynamics—An aid for clinical research and graduate education", (Springer, New York), 2005, 8 pages.

Wilkinson I.B., et al., "Pulse Wave Analysis and Arterial Stiffness", Journal of Cardiovascular Pharmacology, 1998, vol. 32 (Supp) 3), pp. S33-S37.

International Search Report and Written Opinion—PCT/US2015/016701—ISA/EPO—dated Jul. 7, 2015.

* cited by examiner

(PRIOR ART)

FIG. 9

METHOD FOR DETERMINING PULSE WAVE VELOCITY IN AN ARTERY

RELATED APPLICATIONS

This application claims the benefit of U.S. Provisional Patent Application 61/943,777 entitled "Method for Determining Pulse Wave Velocity in an Artery," filed Feb. 24, 2014, the entire contents of which is hereby incorporated by reference for all purposes.

BACKGROUND

A Pulse Wave Velocity (PWV) is a relevant indicator of the condition of an arterial system of an individual. The PWV is the propagation velocity of the pressure pulse or the velocity pulse of blood along an artery initiated by the contraction of the left ventricle of the heart. The propagation velocity of the velocity pulse is generally similar to the propagation velocity of the pressure pulse, but the shape and phase are slightly different. In order to measure the PWV, the motion of the pulse in the artery is typically observed via some form of sensor arrangement. Different sensor arrangements may be used for measuring the pressure pulse versus the velocity pulse. Since the dominating pressure modes relate to deformations of the arterial wall perpendicular to the direction of the wall, observing the deformations of the arterial wall may give an indication of the motion of the pulse. While other pressure modes also exist, such as longitudinal pressure fluctuations both in the wall and in the fluid itself, observing the deformations of the arterial wall perpendicular to the direction of the wall will in most cases give a good identification of the motion of the pulse.

The pulse wave velocity may be estimated by placing two sensors along an artery with a known spacing l, recording pulses at the positions of both sensors, and estimating the temporal displacement of one pulse value relative to the other pulse value. This estimation yields a transit time tt. The ratio of l/tt gives an estimate of the Pulse Wave Velocity. While such methods may be used across long lengths, such as from near the heart to an outer extremity or from the carotid artery to the femoral artery, in many cases, it is desired to know the PWV at a specific location, such as a forearm. PWV measurements taken using a relatively short span between sensors (e.g., across a portion of the forearm) are referred to herein as the "local PWV."

Traditional direct measurements for determining PWV, and especially local PWV, are often not repeatable or are at least associated with unacceptable levels of uncertainty (i.e., the standard deviation meets or exceeds the mean). This fact is especially pronounced with devices that impose a minimum of interference with the subject (e.g., devices that do not applying substantial pressure that deforms the arterial wall). While minimizing interference with the subject is important because disturbances to the subject may by themselves impose a change in PWV, conventional non-interfering PWV measuring techniques are not generally reliable.

SUMMARY

The various embodiments include a method of determining an estimated pulse wave velocity of an artery of a subject. Embodiment methods may include applying a series of counter pressures, measuring a first parameter related to pulse wave velocity, estimating a second parameter in a model, and determining the estimated pulse wave velocity. The series of counter pressures may be applied at a set location on the subject over the artery with a pressure device. Each of the series of counter pressures may be different from one another, applied at the set location, and between zero and a diastolic pressure of the subject. The first parameter may be measured when each of the series of counter pressures is applied. The model for estimating the second parameter may establish a relationship of the first parameter measured to each of the series of counter pressures. The estimated pulse wave velocity may be determined based on the second parameter estimated in the model.

In some embodiments, the series of counter pressures may each apply pressure perpendicular to a longitudinal direction of a limb containing the artery. The first parameter may be measured using two sensors disposed between the tightening band and a portion of skin of the subject. The two sensors may be disposed on a portion of skin of the subject and outside opposed ends of the tightening band. An ultrasound sensor may be embedded inside the tightening band. Additionally or alternatively, two sensors may be separated by a span along the artery to measure a transit time of a pulse between the two sensors. The first parameter may also be measured by measuring across a span of less than 20 cm at the set location, wherein the series of counter pressures are each applied along the span. Measuring the first parameter may include detecting a distension of the artery over time and/or measuring a first set of parameters. The first parameter may be measured using a technology selected from the group consisting of tonometry, ultrasound, nuclear magnetic resonance, a propagation property of electro-magnetic waves, an optical measurement, and bioelectrical impedance. The second parameter estimated in the model may include a second set of parameters.

In some embodiments, the method may further include selecting the model from a predetermined set of models based on a best fit of the model to the first parameter measured at each of the series of counter pressures. The model may be selected from a predetermined stress-strain relationship of the artery, a Bramwell-Hill equation, an exponential model, and a bi-linear model. Among the series of counter pressures, higher counter pressures may be weighted more heavily than lower counter pressures when calculating the second parameter.

Further embodiments may include a computing device having a processor configured with processor-executable instructions to perform various operations corresponding to the methods discussed above.

Further embodiments may include one or more computing devices having various means for performing functions corresponding to the method operations discussed above.

Further embodiments may include a non-transitory processor-readable storage medium having stored thereon processor-executable instructions configured to cause a processor to perform various operations corresponding to the method operations discussed above.

BRIEF DESCRIPTION OF THE DRAWINGS

The accompanying drawings, which are incorporated herein and constitute part of this specification, illustrate example embodiments, and together with the general description given above and the detailed description given below, serve to explain the features of the invention.

DETAILED DESCRIPTION

Various embodiments will be described in detail with reference to the accompanying drawings. Wherever possible the same reference numbers will be used throughout the drawings to refer to the same or like parts. References made to particular examples and implementations are for illustrative purposes, and are not intended to limit the scope of the invention or the claims.

Various embodiments include a method of estimating the PWV with less uncertainty than conventional methods used for determining local PWV. In accordance with various embodiments, a multi-step process may be used to derive a more accurate estimation of the PWV for a relatively short or long portion of an artery. The estimated PWV in accordance with various embodiments may be used to provide indicators of the condition of the arterial system.

Various embodiments include a method of determining an estimated PWV, with no applied counter pressure, in an artery of a subject. The method may include applying a series of counter pressures over the artery of the subject. A parameter related to the pulse wave velocity may be measured when each of the series of counter pressures are applied. In addition, the method may include calculating an unknown parameter in a select model and determining the estimated PWV based on the determined unknown parameter. Each of the series of counter pressures may be applied by the same pressure device in the same location, but individual counter pressures within the series may have different magnitudes. In addition, each of the series of counter pressures may be applied at the same set location. Also, the counter pressures may be between zero and the diastolic pressure of the subject. The unknown parameter may be calculated in the select model, which establishes a relationship of the parameter to counter pressure.

As used herein, the term "counter pressure" refers to the pressure force applied when something presses or pushes against an outer wall of an artery, in a way that the applied pressure force or effects of the applied pressure force may be measured and/or evaluated. As used herein, the term "pressure force" refers to a force associated with a given pressure, which may have a general direction. A counter pressure may be derived from an external pressure force, applied to a portion of skin of a subject, pressing an artery there under. The pressure force from a counter pressure may be generally perpendicular to a longitudinal extent of an artery.

As used herein, the term "model" refers to a mathematical representation of a state of a system or process that may be used to calculate at least one unknown parameter. A number of different models may be available for comparison so an appropriate model or the best-fit model may be selected.

PWV is often measured over longer stretches of artery (e.g. from the carotid artery to the femoral artery). Using a long propagation path for the pulse may reduce the effects of uncertainties in the temporal location of pulses. However, the pulse shape tends to change over a long propagation path, which increases the uncertainty of local PWV estimated using conventional methods PWV if measured over a long propagation path.

The systolic part of the measured pulse of a subject may typically have a duration of approximately 0.1 second. The propagation velocity in the aorta may be, for example, 5 m/s while the propagation velocity in the peripheral system may be, for example, 10 m/s. Thus, the spatial length of a pulse (for the systolic part of the pulse) is typically about 0.5 m near the aorta and about 1 m in the peripheral system. The time between consecutive pulses typically is slightly less than one second, and thus the distance through the peripheral system between the start of one pulse and the start of the next pulse is typically about 10 meters. This implies that a single pulse is typically active over a relatively long stretch. If the peripheral system is modeled as a hypothetical infinitely long vessel with a constant diameter, a thin wall, and a fixed elastic modulus, the propagation of pulses may be modeled as a relatively simple physical phenomenon. Under such a model, it would be relatively simple to measure the distance between two pulses traveling through the system.

However, a simple linear model is inappropriate because arterial systems are generally very complex and highly nonlinear. For example, arteries are generally tapered, their wall thicknesses are not small compared to the diameter, and the spatial length of individual pulses are comparable to the characteristic lengths of arteries in limbs. Further, a large number of discontinuities may typically be encountered at bifurcations in the arterial system. Discontinuities in arterial systems include changes in arterial properties on a length scale that is shorter than the spatial length of a pulse or smaller than the wavelength of any relevant spectral components of the pulse. The resultant shape of a typical pulse may thus change as it propagates through the arterial system. For example, the pulse shape may change because the propagation velocity depends on vessel dimensions as well as on the elastic modulus of the vessel. The diameter of arteries tend to become smaller with distance from the heart, and the elastic modulus of the vessel depends on the vessel distension. In addition, pulse shape may change from the effects of reflections that occur when a pulse wave encounters a discontinuity in vessel geometry.

Figure 9:
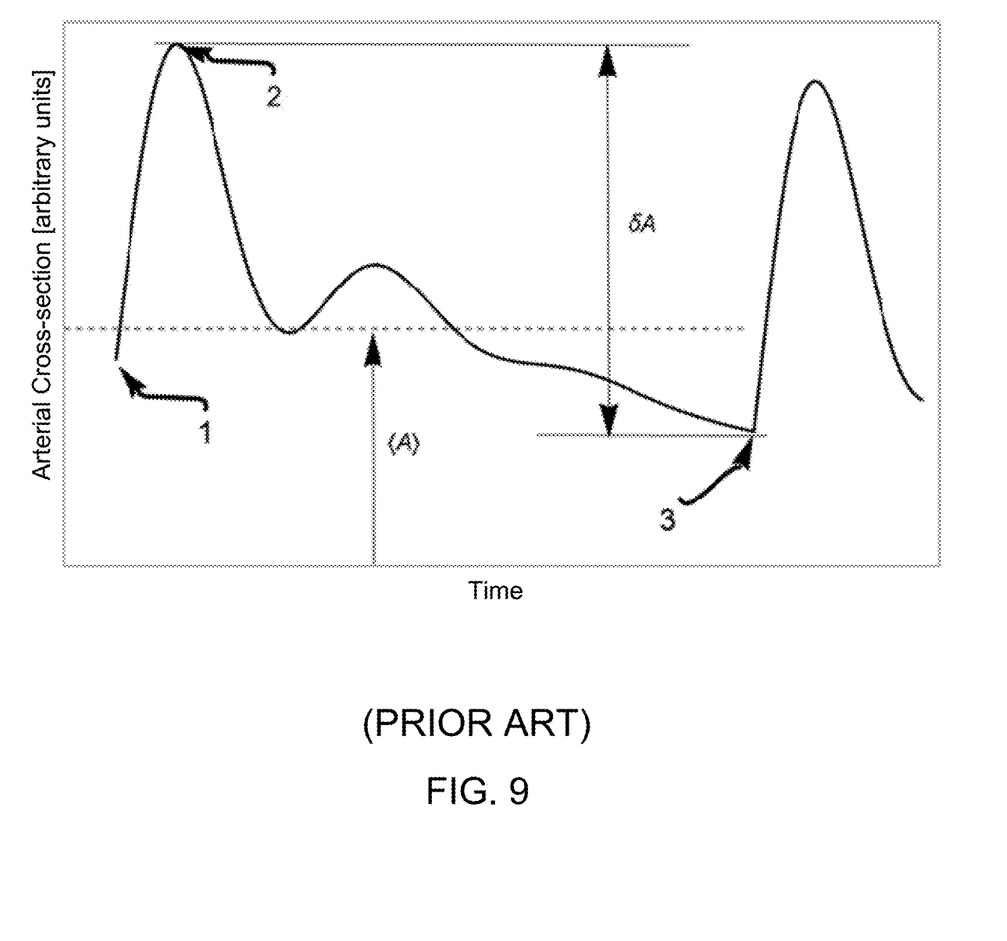
FIG. 9 is a graph of a cross-section of an artery over time representing a pulse.

FIG. 9 shows a graph of a typical pulse shape, with the vertical axis reflecting an arterial cross-sectional area, using arbitrary units, and the horizontal axis representing time, which may be measured in one or more seconds. The location within the arterial system where pulse detection is performed may determine the shape of a pulse that is measured. Further, the pulse shape may depend on the state of the subject providing the measurement. Such variables may contribute to uncertainty in the estimation of the temporal pulse location. Thus, in order to promote consistency, the onset of a pulse right after the end of the diastolic period may be used as the "trigger mark." At the start of a new pulse (indicated as "1" in FIG. 9), the pressure in the artery starts rising quickly, which causes distension of the blood vessel (i.e., an increase in the cross-sectional area of the blood vessel). A peak of the pulse (indicated as "2" in FIG. 9) reflects the systolic pressure. Thereafter, at an end of the pulse (indicated as "3" in FIG. 9), the pressure again drops to the diastolic pressure. The quick rise in pressure after a period of lower pressure (i.e. the transition between the diastolic period and the systolic period) is a characteristic portion of the pulse. As such, the trigger mark may be more consistently identified when measuring a pulse. This trigger mark may be used to measure the temporal separation between pulses.

Measurements of PWV made using conventional techniques typically have significant uncertainty. In particular, measurements have significant uncertainty when measured in the peripheral system across a span that is shorter than the characteristic spatial length of the systolic part of the pulse. In addition, the low frequency parts of the pulse generally propagate with a different velocity than the high frequency parts. Further, the propagation velocity of the high frequency parts may be particularly relevant to vascular physiology. As such, it may be advantageous to apply a high-pass filter to the measurements used to identify the pulse that filters out the low frequency portions and keeps the high frequency portions. For example, the initial quick rise of the pressure pulse is a high frequency component, which may be retained and accentuated after the filtering. In addition, it may be advantageous to determine instances from those parts of a signal when the temporal gradients are largest.

Figure 1:
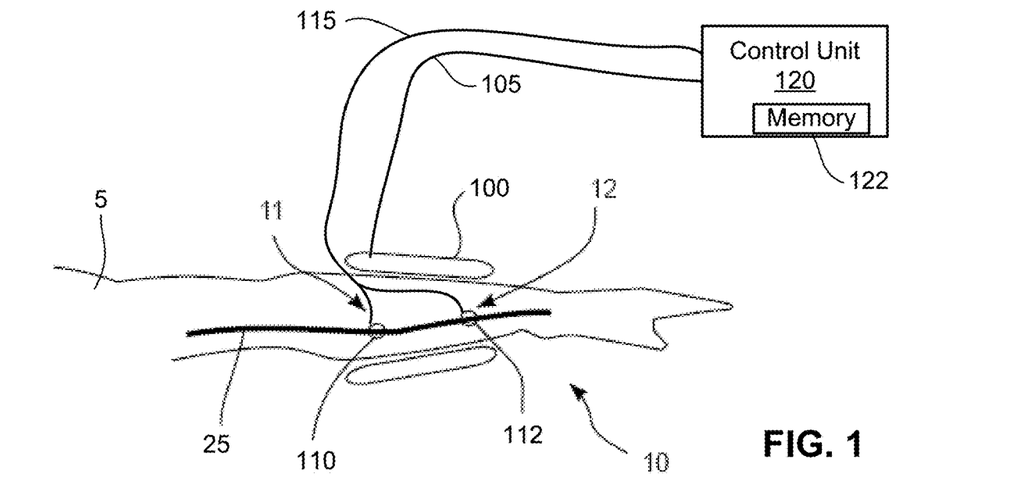
FIG. 1 is a schematic diagram of a device for determining an estimated pulse wave velocity including two sensors and a tightening band according to various embodiments.

FIG. 1 illustrates an apparatus 10 configured to determine an estimated PWV in an artery of a subject 5 in accordance with various embodiments. The apparatus 10 may include a pressure device 100 for applying counter pressures, a sensor 110 for measuring a first parameter, and a control unit 120 coupled to the pressure device and the sensor for processing data.

In various embodiments, the pressure device 100 may cover a set location on the subject 5 being measured (i.e., a select portion of the subject's body). For example, the pressure device 100 may be a tightening band, such as an inflatable cuff, that may cover part of a limb and apply pressure to that part of the limb. The pressure device 100 may wrap completely around a limb of the subject 5. In FIG. 1, the pressure device 100 is shown in cross-section, so portions are illustrated on opposite sides of a limb of the subject 5. Additional types of pressure devices may be used in accordance with various embodiments.

A control unit 120 may be included that registers pressure levels applied by the pressure device 100 and measurements from the sensor 110. Values from pressure and sensor measurements may be stored in a memory 122. In addition, the control unit 120 may regulate and/or control the timing and/or pressure levels applied by the pressure device 100. Further, the control unit may include one or more processors configured to make intermediate and/or final calculations and determinations regarding PWV estimates. While the control unit 120 is illustrated as a single unit, multiple control units may be provided. In addition, although connections 105, 115 are illustrated as wired connections, the control unit 120 may include wireless connections, such as using one or more wireless transceivers and antennas.

The sensor 110 may include more than one sensor, such as one sensor 110 positioned at a first location 11, and another sensor 112 positioned at a second location 12. The first and second locations 11, 12 may be selected to be roughly aligned along a path of an artery 25 of the subject 5. The two sensors 110, 112 may be placed at the two locations 11, 12 and configured to provide signals proportional to either the pulse pressures or the velocity pulses. By using a tightening band as the pressure device 100, the two sensors 110, 112 may be disposed between the pressure device 100 and the skin of the subject 5. This configuration may be desirable since the spacing over which the transit time of the pulse is measured will have a generally uniform counter pressure. Alternatively, the sensors 110, 112 may be arranged outside and on opposed ends of the tightening band (i.e., on the skin outside the tightening band, directly before and after the tightening band. This alternative may be useful in certain configurations, depending upon the type of sensor used, where it may not be possible to arrange the sensors directly under the pressure device 100.

Various embodiments include sensors exploiting bioelectric impedance variations. An advantage of using sensors exploiting bioelectric impedance variations is that the sensors themselves may be relatively "flat" and flexible. In this way, such sensors may be easily arranged underneath the tightening band, on the skin of the subject, without significantly altering the counter pressure being applied in the region. Further, the subject may experience little or no discomfort due to such sensors, even when the tightening band is an inflatable cuff and is fully inflated.

The apparatus 10 may apply a series of counter pressures to the subject 5. The pressure device 100 may control and appropriately vary the counter pressure being applied. In addition to the tightening band, the pressure device 100 may include a pressure gauge, a tensioning device, and/or a pumping device. Alternatively, the pressure gauge, the tensioning device, and/or the pumping device may be part of the control unit 120. In various embodiments, the counter pressure may be varied in a range from zero to the diastolic pressure of the subject on which measurements are performed. A first connection 105 may couple the pressure device 100, or components thereof, to the control unit 120 for recording the level of pressure being applied to the subject 5 at a particular time. The first connection 105 may be a wire and/or tubing configured to provide the control unit 120 a suitable indication of the pressure(s) being applied to the subject 5. In addition, the control unit 120 may include a processor for controlling the pumping device and thus the amount of pressure applied when measurements are taken.

The apparatus 10 may measure transit time of a pulse as it travels between the two sensors 110, 112, which is a parameter related to the pulse wave velocity. The time it takes for a pulse to pass between the two sensors 110, 112 may be a measure of the transit time of a pulse, which is associated with the contraction of the left ventricle of the heart. The distance between the first location 11 and the second location 12 may be a known length over which a series of counter pressures are applied in accordance with various embodiments. A second connection 115 may couple the two sensors 110, 112 to the control unit 120. In this way, the measured transit time between the two sensors 110, 112 may be measured and/or recorded by the control unit 120. Such transit time measurements may be recorded over a series of different counter pressures. The series of counter pressures may vary by a fixed amount (e.g., 10-20 mmHg) or other increments. In various embodiments, the counter pressures may range from zero to the diastolic pressure of the subject. Counter pressures higher than the diastolic blood pressure of the subject may not be desirable because the transmural pressure might fall below zero, which may risk collapsing the artery for a portion of the pulse. A collapsing or unstable artery may undermine the assumptions used in modeling the arteries, and thus make the any determinations regarding PWV less reliable. However, counter pressure values slightly in excess of the diastolic blood pressure may result in measurements that are reliable.

Figure 2:
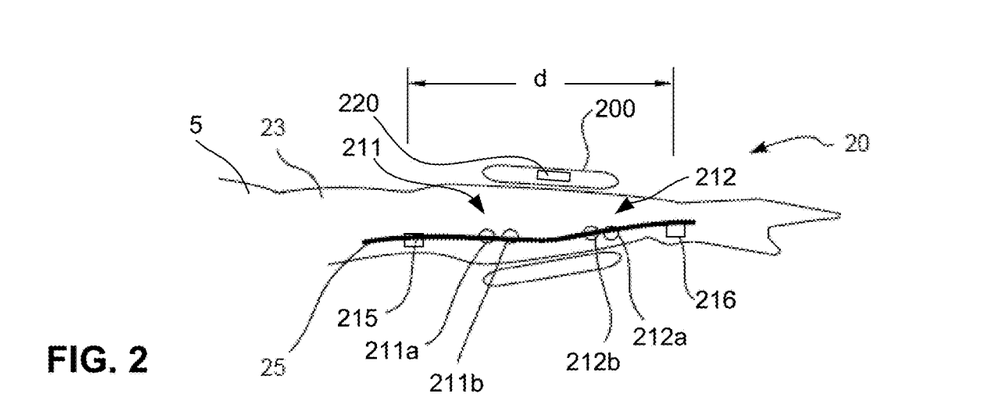
FIG. 2 is a schematic diagram of a device for determining an estimated pulse wave velocity including additional sensors according to various embodiments.

FIG. 2 illustrates an apparatus 20 configured to determine an estimated PWV in an artery of a subject 5 in accordance with various embodiments. The apparatus 20 may include a pressure device 200 for applying counter pressures, a first sensor 211 and a second sensor 212 for measuring one or more parameters using bioelectric impedance, and a control unit 220 coupled to the pressure device and the sensors for processing data. The first sensor 211 may include a first outer detection electrode 211a and a first inner detection electrode 211b. Similarly, the second sensor 212 may include a second outer detection electrode 212a and a second inner detection electrode 212b. The detection electrodes 211a, 211b, 212a, 212b may be disposed on a portion of skin of an arm 23, under and just outside the pressure device 200. In this way, an outer two detection electrodes 211a, 212a may be disposed just outside opposed ends of the pressure device 200, while an inner two detection electrodes 211b, 212b may be disposed under the pressure device 200. In addition, two excitation electrodes 215, 216 may also be applied to the skin of the arm 23 much further outside the pressure device 200 than outer two detection electrodes 211a, 212a. In particular, the excitation electrodes 215, 216 may be spaced apart by a separation distance d considerably larger than the depth at which the artery 25 is embedded in the arm 23. The separation distance d may extend beyond the forearm, for example from the wrist to the elbow (e.g., approximately 10 cm). Alternatively, the separation distance d may extend further, such as the length of most of the limb.

Figure 3:
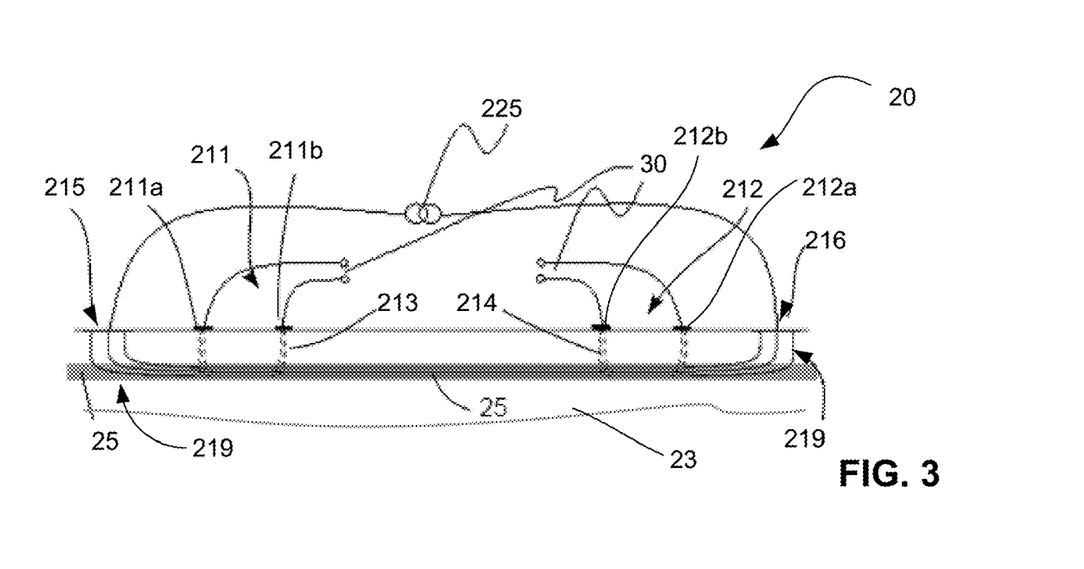
FIG. 3 is a schematic diagram of a sensor arrangement according to various embodiments.

FIG. 3 illustrates a schematic diagram of the workings of the sensor arrangement of the apparatus in FIG. 2. In some embodiments, a current generator 225 may generate a current that oscillates at a particular frequency. The current generator 225 may be located near the subject (not shown) or inside a control unit (e.g., 220 in FIG. 2). A current from the current generator 225 may be directed into the subject (e.g., into the arm 23) through the excitation electrodes 215, 216. The current from the current generator 225 may be at a frequency in the range of 10 kHz to 10 MHz, or higher. The magnitude of the current may be, for example, in the range of 0.005 mA to 10 mA. The excitation electrodes 215, 216 may be almost any shape, including a rectangular, oval, or annular shape. In addition, the excitation electrodes 215, 216 may be sized appropriately to the body part on which they may be applied. For example, the excitation electrodes 215, 216 may have an overall diameter of approximately 5 mm to 20 mm. In various embodiments, the excitation electrodes 215, 216 may have a width perpendicular to an underlying artery that is larger than a length in the longitudinal direction of the artery since the exact path of the artery may be unknown (e.g., displaced to one side or another). The oscillating current from the current generator 225 may generate excitation field lines 219, which near the skin will extend essentially perpendicular to the skin surface. As the excitation field lines 219 extend away from the skin, because the skin and the subcutaneous fat have low conductivities, the excitation field lines 219 become more aligned with the longitudinal direction of the artery 25 because blood has higher conductivity. Thus, close to and inside the artery 25 the excitation field lines 219 become aligned with the direction of the blood inside the artery 25.

The outer detection electrodes 211a, 212a may be separated from their corresponding paired inner detection electrode 211b, 212b by a distance comparable to the expected entrenchment depth of the artery 25 (i.e., a distance approximately equal to how deep under the skin the artery is expected to be). For example, the spacing between the first outer detection electrode 211a and the first inner detection electrode 211b may be from a few millimeters to 5 centimeters, depending on the location on the subject and the specific anatomy of the particular subject. A similar spacing may be established between the second outer detection electrode 212a and the second inner detection electrode 212b. The detection electrodes 211a, 211b, 212a, 212b may be almost any shape, including rectangular, oval, or annular, and may be sized appropriately to the body part on which they will be applied, similar to the shapes and sizes noted above for the excitation electrodes 215, 216. For example, the detection electrodes 211a, 211b, 212a, 212b may have an overall diameter of approximately 1 mm to 20 mm. The sensors 211, 212 may also generate virtual field lines 213, 214 that may overlap the excitation field lines 219. The overlaps in the virtual field lines 213, 214 and the excitation field lines 219 may define the effective detection regions, from where impedance variations may be measured by the sensors 211, 212. The signals from the sensors 211, 212 may be recorded and analyzed by a processor 30, such as one contained in the control unit (e.g., 220). In the apparatus 20, only the sensors 211, 212 that are used for detection are placed in the region where a counter pressure is applied by the pressure device (e.g., 200).

A demodulation of the signals from the sensors 211, 212 may be performed by quadrature detection. In quadrature detection, the detected signals may be mixed with quadrature components of a reference signal derived from the same oscillator that provides the excitation signal to the arm 23 of the subject 5. In general an in-phase part of the demodulated signal may typically be the dominant part reflecting the fact that the real part of the detected impedance is dominating. However, the quadrature component may also be detected and a weighted quadratic sum of the in-phase and quadrature components, respectively, can be applied in order to enhance detection efficiency in cases where the imaginary part of the impedance is considered important. The imaginary part may be associated with the real parts of the dielectric constants of the relevant tissues, which normally are constituted by skin, fat, muscles, and blood. The signals can advantageously be filtered in order to minimize the effect of noise but also to enhance those parts of the signal that are most important for timing: i.e. those parts with a large temporal gradient. The filters for the sensors 211, 212 may have identical phase characteristics in order to avoid any bias in the estimation of the transit time. Digital finite impulse response filters may be used since the phase characteristics may be accurately controlled due their sampling frequency (e.g., 5 kHz).

The outputs of the signals from the sensors 211, 212 may reflect the distension of the artery at the two sensor locations and would in general show the pulse shape over time, including the effects of any filtering. Measurements at two or more times (i.e., different time stamps) may reflect the pulse shape. Assuming that a detailed calibration is not performed on the sensor outputs, the outputs of the sensors may be equal to the distension directly, but may be proportional to the distension. Direct readings of distension may not be necessary, since it is the timing of the pulses that is of interest. Nonetheless, calibration may be performed for measuring the distension directly from the sensor outputs.

In an embodiment, once the pulse shapes are obtained by demodulation of the signals measured by the sensors 211, 212, the transit time may be determined based on the timing of single pulses. In an embodiment, the temporal start of a pulse may be defined by the time at which the high-pass filtered signal passes the zero-level. In another embodiment, the temporal start of the pulse may be defined by the time at which the maximum upward slope of the distension is detected. In a third embodiment the temporal start of a pulse is defined as the time at which the minimum distension occurs plus half the time to the maximum distension point (max/min) All three embodiments yield similar results. However, the max/min method appears less sensitive to broadband noise, whereas the zero-crossing method is less affected by reflections affecting the last part of the systolic phase and/or affecting the diastolic phase. The zero-crossing method is simpler to implement than the maximum gradient method. However, the maximum gradient method yields a slightly better estimation of the pulse position if broadband noise is negligible.

In another embodiment, the transit time may be estimated from a short-term cross-correlation of the filtered signals. This method may be robust and lend itself to an efficient validation of the signals. However, timing performed on individual validated pulses may be preferable in order to overcome or minimize the effects of pulse reflections in the arterial system and in order to reject erroneous pulse measurements caused by subject movements that are not related to the heartbeat. Reflections and movements often affect the pulse shape quite considerably. In addition, while the effect of reflections on the very first part of the pulse—the systolic upstroke—are generally assumed to be small, the various embodiments may be used to demonstrate the effect of reflections may have a bigger impact than previously thought.

Various types of devices may be used to measure a parameter related to the pulse wave velocity while a pressure is applied to the subject. Some examples include devices that employ a technology such as tonometry, ultrasound, nuclear magnetic resonance, propagating electro-magnetic waves, optical sensing, and/or bioelectrical impedance. Tonometry measures fluid pressure, such as a localized blood vessel pressure. Ultrasound may be used to measure distension of an artery wall or flow velocity (i.e., a Doppler velocimetry). Nuclear magnetic resonance may also be used to measuring distension. Other techniques include various devices capable of detecting a propagation property of electro-magnetic waves. In addition, optical instruments may be used to detect and measure distension (e.g. photoplethysmography) or flow velocity. As described above with regard to FIGS. 2 and 3, bioelectrical impedance may be measured, particularly in applications where distension or flow velocity may be detected from the bioelectrical impedance variations. Additional devices suitable for measuring one or more parameters related to pulse wave velocity may be used in accordance with various embodiments.

Figure 4:
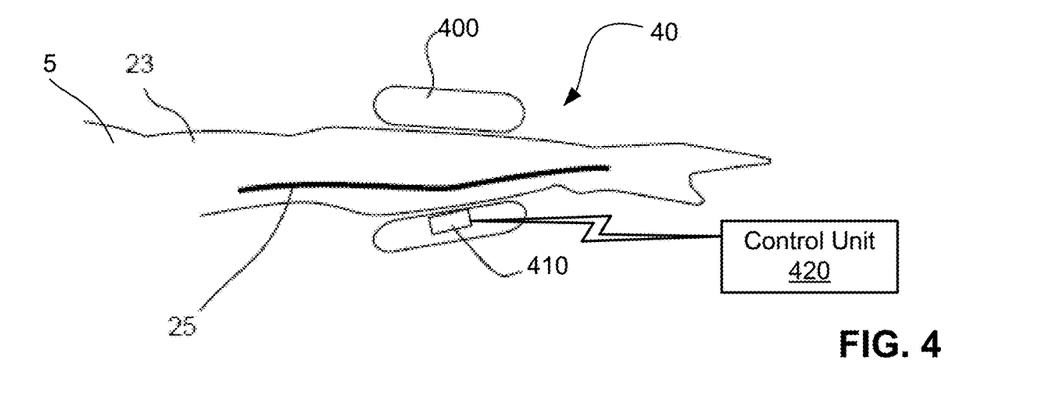
FIG. 4 is a schematic diagram of a device for determining an estimated pulse wave velocity including an ultrasound sensor and wireless connections according to various embodiments.

FIG. 4 illustrates an apparatus 40 configured to determine an estimated PWV in an artery 25 of a subject 5 in accordance with various embodiments. The apparatus 40 may include a pressure device 400 for applying counter pressures, a sensor 410 for measuring the parameter(s), and a control unit 420 wirelessly coupled to the pressure device 400 and the sensor 410 for processing data. The apparatus 40 integrates the sensor 410 into the pressure device 400.

The sensor 410 may use ultrasound, tonometry, optical sensing, bioelectric impedance, or other sensing principles. The pressure device 400 may be an inflatable cuff with the sensor 410 arranged inside a bladder of the cuff In this way, the pressure device 400 may be inflated without sandwiching the sensor 410 between an inside of the cuff and the skin on the arm 23 on which the pressure device 400 is mounted.

The sensor 410 may be integrated into the inside outer surface of the pressure device 400 (i.e., configured to face the subject's skin when worn thereon), which presses against the skin. In this way, a firm and even engagement between the skin and the sensor may be maintained. In addition, the sensor 410 may be a bulkier sensor without causing discomfort to the subject.

Figure 5:
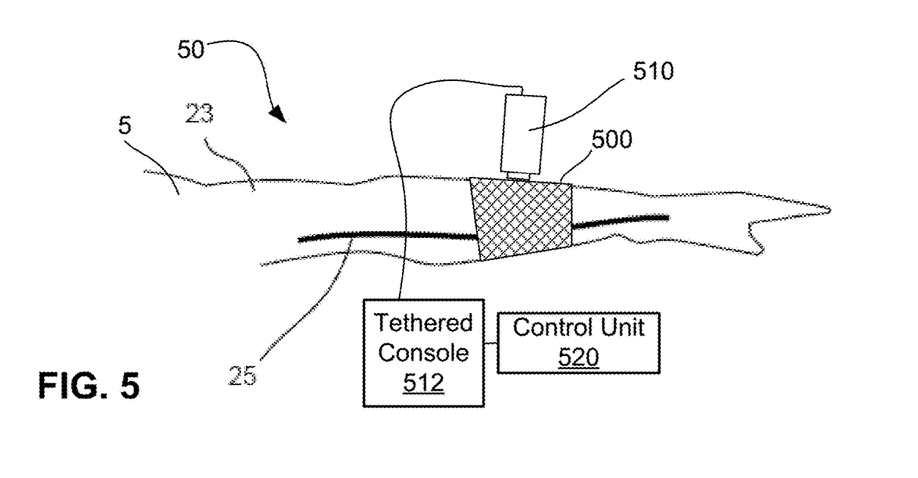
FIG. 5 is a schematic diagram of a device for determining an estimated pulse wave velocity including an alternative sensor and pressure straps according to various embodiments.

FIG. 5 illustrates an apparatus 50 configured to determine an estimated PWV in an artery of a subject 5 in accordance with various embodiments. The apparatus 50 may include a pressure device 500 for applying counter pressures, a manually operated sensor 510 for measuring the parameter(s), and a control unit 520 coupled to the pressure device and the sensor for processing data.

The sensor 510 may use ultrasound, tonometry, optical sensing, or other sensing principle. The sensor 510 may be a manually operated (i.e., hand-held) device, which may be easily moved from one set position on the arm 23 to another. The sensor 510 may include a tethered console 512 with a processor, memory, and additional components supporting the function of the sensor 510. The sensor 510, via the tethered console 512, may be directly coupled to the control unit 520 for communicating data regarding the sensor measurements.

The pressure device 500 may include a tightening band in the form of one or more fabric sleeves applied around the arm 23 of the subject 5, which may be tightened to various levels of tightness. In some embodiments, multiple sleeves may be layered over one another to form all or part of the pressure device 500. The pressure device 500 may be configured with a pressure-measuring element (e.g., a strain gauge) and a display, indicating a value for the pressure applied to the subject 5. Such indicated pressure values may be manually entered in the control unit 520 for correlation to any measurements taken by the sensor 510. Alternatively, a wired or wireless connection (not shown) may be provided for communicating pressure values between the pressure device 500 and the control unit 520. The pressure-measuring element in the tightening band may measure tension therein, which is different from a counter pressure, which is a pressure force applied toward and/or against the artery 25. Nonetheless, the tension in the tightening band may be related to the counter pressure via a monotonic function or a proportional function. For example, the counter pressure Pc may be equal to the tension T applied by one or both sleeves, multiplied by a constant K1 (i.e., Pc=K1×T). The constant K1 may depend on characteristics of the pressure device 500 and how it engages the subject 5. Such a constant K1 may be determined or estimated a priori and used to convert instant tension T readings into counter pressure Pc readings. Other devices for applying a counter pressure may be used in accordance with various embodiments.

Alternatively, the counter pressure applied by the tightening band of the pressure device 500 may not be immediately known (i.e., not measured directly by the pressure device 500 or the control unit 520). This may thus present more than one unknown parameter (i.e., a set of unknown parameters) in the model selected for calculation the unknown parameter(s) used for the determination of the estimated PWV. As a further alternative, if the selected model is an empirical model, the strain gauge reading may be used directly instead of the counter pressure. As a further alternative, if the selected model is based on physical principles, the strain gauge reading may be converted to the counter pressure via other estimation techniques.

Figure 6:
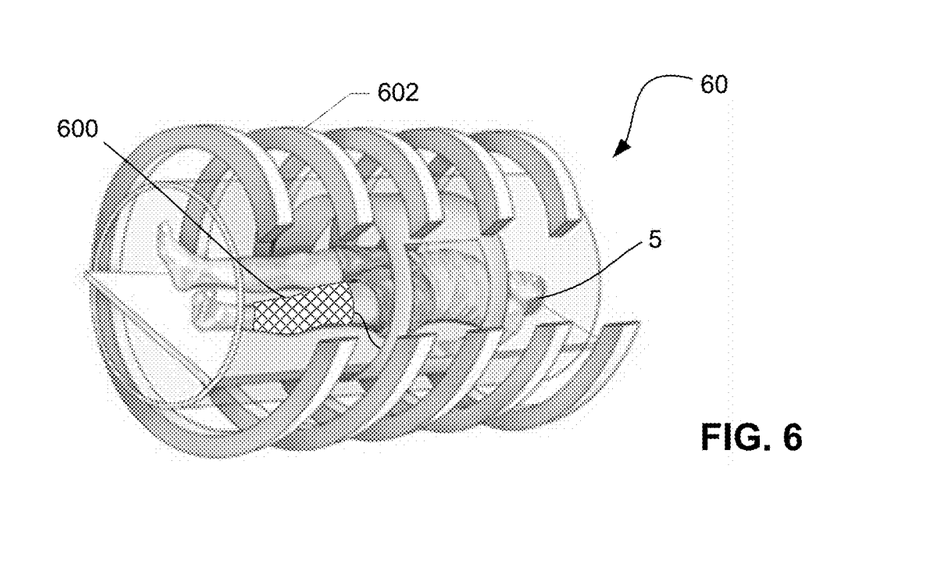
FIG. 6 is a perspective view of a device for determining an estimated pulse wave velocity using nuclear magnetic resonance measuring a subject's leg according to various embodiments.

FIG. 6 illustrates an apparatus 60 configured to determine an estimated PWV in an artery of a subject 5 in accordance with various embodiments. The apparatus 60 may include a pressure device 600 for applying counter pressures, a sensor 610 in the form of a nuclear magnetic resonance machine 602 for measuring one or more parameters. For example, the nuclear magnetic resonance machine 602 may measure distension and/or flow pulses in an artery. A control unit (not shown) may be integrated into or be a part of the nuclear magnetic resonance machine 602 or be a separate device.

The pressure device 600 is shown strapped onto a leg of the subject 5. In this way, both the leg and the pressure device 600 are inside the nuclear magnetic resonance machine 602 during operation of the machine. The pressure device 600 may be directly connected to the inside of the nuclear magnetic resonance machine. In addition, the pressure device 600 may be configured to meet special compatibility requirements in order to be used inside the nuclear magnetic resonance machine 602.

In various embodiments, one or more of the pressure device (e.g., 100, 200, 400, 500, 600), the sensor(s) (e.g., 110, 211, 213, 410, 510), and the control unit (e.g., 120, 220, 420, 520) may be integrated into a single device or separated into multiple devices. For example, an inflatable cuff may be provided with detection electrodes or other sensors fastened on an inner engagement surface, avoiding the need to separately mount the sensors.

In various embodiments, the pressure device(s), the sensor(s), and/or the control unit(s) may include one or more processors. Such processors may be any programmable microprocessor, microcomputer or multiple processor chip or chips that can be configured by software instructions (applications) to perform a variety of functions, including the functions of various embodiments described above. In some devices, multiple processors may be provided, such as one processor dedicated to sensor or pressure readings, calculations, or communication functions and one processor dedicated to running other applications. Typically, software applications may be stored in the internal memory (e.g., 122 in FIG. 1) before they are accessed and loaded into the processor(s). The processor(s) may include internal memory sufficient to store the application software instructions. In many devices, the memory may be a volatile or nonvolatile memory, such as flash memory, or a mixture of both. For the purposes of this description, a general reference to memory refers to memory accessible by the processor(s) including internal memory or removable memory plugged into the control unit and memory within the processor(s) themselves.

Figure 7:
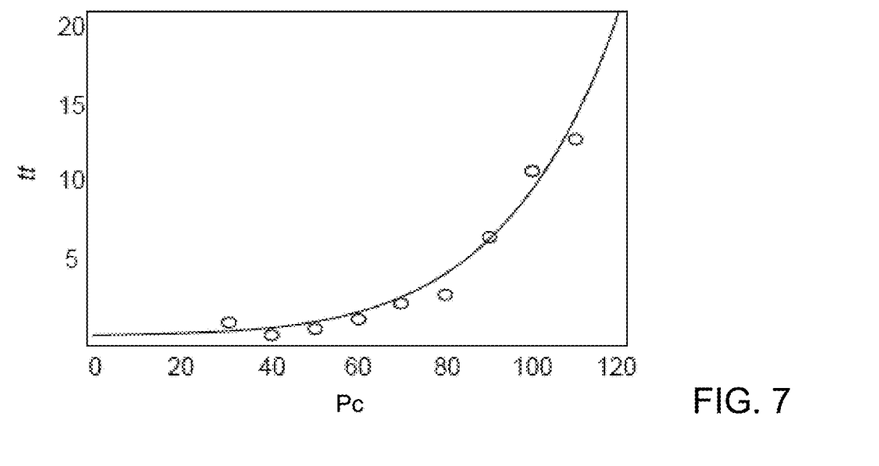
FIG. 7 is a graph of transit times measured at a series of counter pressures according to various embodiments.

FIG. 7 is a graph illustrating data corresponding to values of a series of counter pressures applied to a subject versus the transit times (i.e., a measured parameter) measured at each of those counter pressures. The resulting data points (indicated as circles on the graph) may also be represented as a set of corresponding values of transit time and counter pressure in a data set, such as {tt, Pc}. In various embodiments, a model may be selected that matches the data set of the measured parameter(s) and the corresponding counter pressures.

In various embodiments, the selected model may be generally associated with calculating local PWV values, such as a model based on the Bramwell-Hill equation as follows:

$$v = \sqrt{\frac{dP}{dA} \frac{A}{\rho}}, \quad \text{Eq. 1}$$

where v is the local PWV in the artery, A is the cross sectional area of the artery, $\rho$ is the blood density, P is the transmural pressure and dP/dA is the derivative of the transmural pressure with regards to the area.

The elastic properties of the arterial wall may be highly non-linear. Nonetheless, a general stress-strain relation valid within a typical pressure range of a living being may be expressed by the following non-linear equation relating the transmural pressure and arterial cross-sectional area:

$$P = P_o e^{A/A_o} - 1 \quad \text{Eq. 2,}$$

where P is the transmural pressure, $P_o$ and $A_o$ are parameters, which are dependent on the subject that is being measured, and A is the cross sectional area of the artery being measured, and $P_o$ and $A_o$ are the pressure and cross-sectional area, respectively, of an artery under a non-load condition. The parameters $P_0$ and $A_0$ may be given by the specific elastic properties of the artery being investigated at a particular point in time, since the elastic properties of arteries may change over time. The transmural pressure P may be determined from the pressure differential between the inside and the outside wall of an artery.

Differentiating equation 2 with respect to the cross sectional area A, may provide the following equation:

$$\frac{dP}{dA} = \frac{P_o}{A_o} e^{A/A_o}. \quad \text{Eq. 3}$$

Solving equation 2 for the cross sectional area A, may also provide the following equation:

$$A = A_o \ln\left(\frac{P_o + P}{P_o}\right). \quad \text{Eq. 4}$$

Substituting equation 3 and equation 4 into equation 1 may provide an expression for the local PWV v, which may be based on the parameter $P_o$ and the transmural pressure P. Using the relationship v=l/tt, where l is the spacing between sensors and tt is the transit time, the following relationship between the transmural pressure P and the transit time tt may be derived:

$$tt = \ell \sqrt{\frac{\rho}{(P_o + P)\ln\left(\frac{(P_o + P)}{P_o}\right)}}. \quad \text{Eq. 5}$$

The relationship between transmural pressure P and the transit time tt, as expressed in equation 5, does not include either the cross-sectional area A or the parameter $A_o$ related to the area of the artery.

In addition, the transmural pressure P may be related to the counter pressure $P_c$ in accordance with the following equation:

$$P = \text{MAP} - P_c \quad \text{Eq. 6.}$$

In equation 6, MAP represents the mean arterial pressure without any applied counter pressure. MAP may be determined with various non-invasive devices known in the art or it may be considered as a further unknown parameter.

Inserting equation 6 into equation 5 may yield the following equation:

$$tt = \ell \sqrt{\frac{\rho}{(P_o + MAP - P_c)\ln\left(\frac{(P_o + MAP - P_c)}{P_o}\right)}} \quad \text{Eq. 7}$$

Equation 7 may be selected as a model establishing a relationship of transit time tt (i.e., a measured parameter) to an applied counter pressure $P_c$ (i.e., a known input). While the spacing l and the MAP may be variables in equation 7, the spacing l may be known a priori from the setup of the apparatus taking the measurements (e.g., the spacing between the two sensors). In addition, MAP may be derived from other techniques. Further, variables like the density p may also be known ahead of time (e.g., a value of approximately 1060 kg/m$^3$ may be used as an average density ρ). In this way, a data set providing transit times tt and corresponding counter pressures $P_c$ may leave the one unknown parameter $P_o$ to determine. If equation 7 is selected as the model to be used after a fitting procedure, the unknown parameter $P_o$ may be estimated and used to determine an estimated PWV in accordance with various embodiments.

The model exemplified in equation 7 reflects a physical understanding of the physiological mechanics of arteries, and may thus fit well to various data sets. The model exemplified in equation 7 is based on a predetermined stress-strain relationship in an artery that is exponential (e.g., equation 2). Alternatively, a bi-linear stress-strain relationship may be used to derive a slightly different model establishing a relationship of a measured parameter to the applied counter pressure. Such an alternative version of equation 7, the version of equation 7 presented above, and other models may be part of a predetermined set of models that may be used for estimating at least one parameter and determining an estimated PWV in accordance with various embodiments.

In various embodiments, an empirical model may be used as part of the predetermined set of models. While an empirical model may not be as closely based on the physiological processes occurring in the artery, in certain circumstances an empirical model may be the best fit or an otherwise preferred model based on the data set collected and used. Another model may be based primarily or purely on the data points derived from measurements on the subject. For example, a graphical mapping of the data points may be translated into an equation, which may be suitable as a model for determining an unknown parameter.

Equations 8 and 9 below are examples of other models suitable for explaining a pattern of data collected from measurements and thus suitable for estimating unknown parameters.

$$tt = K_1 e^{K_2 P_c} \quad \text{Eq. 8}$$

$$tt = a + bP_c + c(P_c)^2 \quad \text{Eq. 9}$$

In equation 8 and equation 9, while the transit time tt and the counter pressure Pc are familiar variables, the variables K1, K2, a, b, and c are other unknown parameters that may be determined. Additional equations may be developed and used as suitable models in accordance with various embodiments herein.

Various embodiments estimate one or more unknown parameters in a select model, but the model may be selected based on a data fitting procedure. The data fitting procedure may use techniques for determining how well a particular model fits to an available data set. In this way, the data fitting procedure may determine the best-fitting model as the model that best predicts the values in the data set. Referring again to FIG. 7, the data set {tt, $P_c$} provides values for transit times tt and corresponding counter pressures $P_c$. Using such values, a predetermined set of models, such as the exemplary models discussed above, may be used to determine the model that provides the best fit. In this way, the model providing the best fit to the data set may be selected for estimating the unknown parameter(s).

The fitting procedure may use one or more fitting techniques, such as least squares, weighted least squares (e.g., a fitting where the weighting is proportional to the counter pressure), iterative proportional fitting, matrix ranking, regression analysis, or differential or partial differential equation solutions. In addition, the predetermined set of models may not perfectly fit the data set. Thus, while a best-fit model may be used, additionally the best-fit model may be further enhanced, such as by weighting. For example, among the series of counter pressures, higher counter pressures may be weighted more heavily than lower counter pressure to find and even better fitting model.

Alternative data fitting procedures may consider a set of unknown parameters. For example, in the model according to equation 7, variables like the spacing l or the MAP may not be known parameters a priori (i.e., there values are not known or may not be accurately estimated at the time measurements are taken). Thus in accordance with various embodiments, such further unknown parameters may be estimated using a model selected through data fitting techniques. When the number of data points in a data set exceeds the number of fitting parameters, data models may be more accurately fit.

From the fitting procedure, the unknown parameter(s) in the select model may be calculated. For example, consider a scenario in which equation 7 is selected as the model from a predetermined set of models based on a best fit. In addition, knowing a priori the values for all the known variables, as opposed to the unknown parameter Po, the values from the data set {tt, $P_c$} may be used to estimate a value for the unknown parameter $P_o$.

Once a value has been estimated for the unknown parameter $P_o$, the select model may once again be used. However, this time the estimated unknown parameter $P_o$ and a zero value for the value of the counter pressure $P_c$ may be used. Using a zero value for the counter pressure $P_c$ may reflect conditions when no counter pressure is applied to the arty of the subject. In this way, equation 7 may be reworked to reflect a zero value for the counter pressure $P_c$ as follows:

$$tt = \ell \sqrt{\frac{\rho}{(P_o + MAP)\ln\left(\frac{(P_o + MAP)}{P_o}\right)}} \quad \text{Eq. 10}$$

Having determined a value for the previously unknown parameter $P_o$, equation 10 may be used to determine an estimated transit time tt associated with no external counter pressure applied to the subject. In addition, knowing the spacing l and dividing that spacing l by the estimated transit time may provide an estimated PWV associated with no counter pressure applied to the subject. Such as estimated PWV for zero counter pressure may be different from the PWV that is measured directly at zero counter pressure. Nonetheless, the estimated PWV in accordance with various embodiments may provide a more reliable determination of local PWV, associated with less uncertainty than local PWV measure directly using convention methods.

Figure 8:
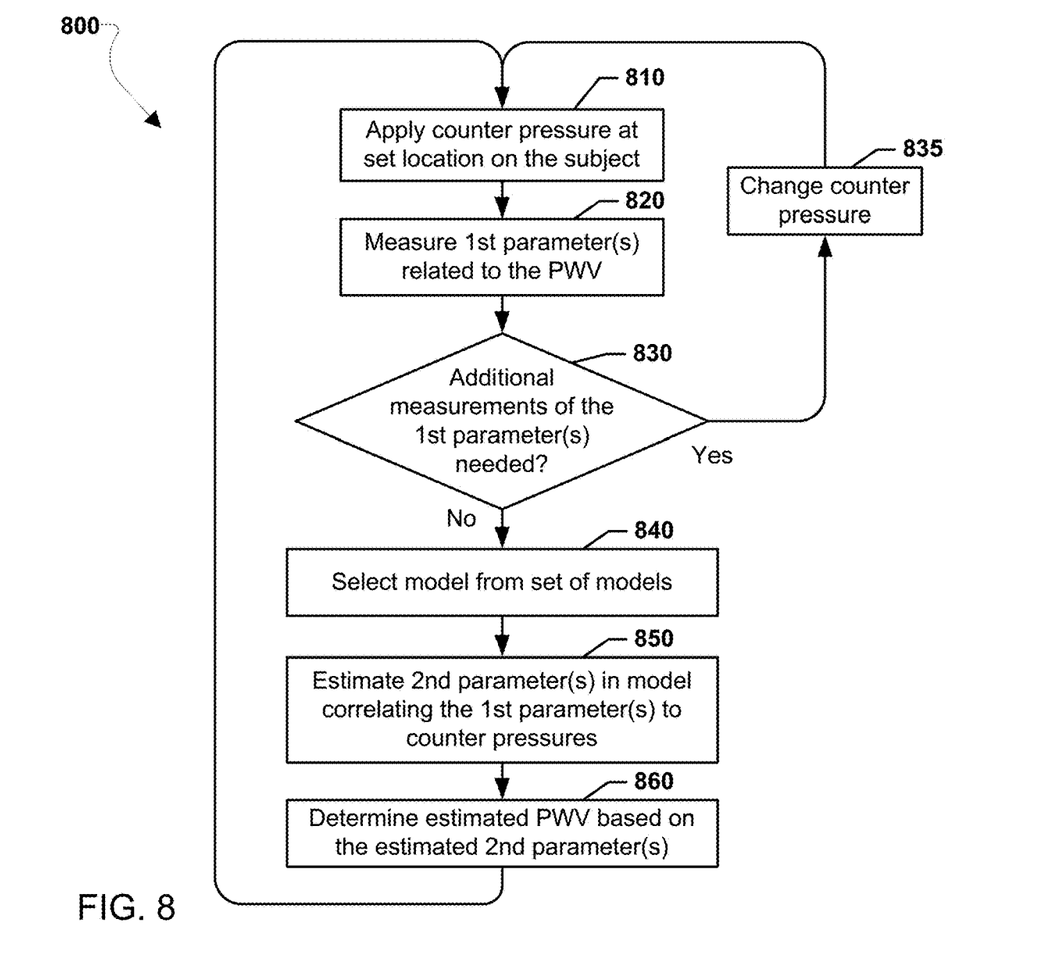
FIG. 8 is a process flow diagram suitable for use in the various embodiments.

FIG. 8 illustrates a method 800 for determine an estimated PWV in an artery of a subject in accordance with various embodiments. Operations of the method 800 may be performed by a pressure device (e.g., 100, 200, 400, 500, 600), one or more sensor(s) (e.g., 110, 112, 211, 213, 410, 510), and a control unit (e.g., 120, 220, 420, 520) or other computing device.

With reference to FIGS. 1-8, in block 810, the pressure device (e.g., 100, 200, 400, 500, 600) may apply a counter pressure at a set location on the subject. The particular pressure device used as the tightening band, such as an inflatable cuff, may limit where on the subject the set location may be. Otherwise, the set location may remain in one place on the subject for a number of different counter pressure applications. The value(s) of the counter pressure applied by the pressure device may be stored in a memory (e.g., memory 122).

In block 820, the sensor (e.g., 110, 112, 211, 213, 410, 510) may measure one or more measureable parameters (i.e., a first parameter) related to the PWV. In various embodiments, the measured parameter is a pulse transit time. However, other parameters may alternatively or additionally be measured in accordance with various embodiments. The measured parameter(s) may be based on recording quantities related to a distension pulse (arterial expansion) or a flow pulse (blood flow velocity variation) at two locations separated by a distance l along an artery. The time from one occurrence to the next may define the transit time tt. Devices may measure distension by using one or more of various principles, such as bioelectric impedance (e.g., impedance-plethysmography), an optical measurement (e.g., optical absorbance or scattering, such as photoplethysmography), ultrasound, and nuclear magnetic resonance. Similarly, the flow pulses may be measured with devices that use one or more of various principles, such as ultrasound, bioelectric impedance (e.g., with detection techniques made sensitive to flow), and/or an optical measurement (e.g., optical differential Doppler or transit time). In addition, other methods may be applied that are based on propagating electromagnetic radiation (e.g. microwaves) exploiting the Doppler Effect or derivatives of nuclear magnetic resonance may also measure flow. The value(s) measured by the sensor may be stored in a memory (e.g., memory 122).

In determination block 830, the control unit (e.g., 120, 220, 420, 520) may determine whether an additional measurement of the parameter(s) is/are needed to determine the estimated PWV. Each measurement collects a data point that may be used for estimating unknown parameters and eventually determining an estimated PWV. The more data points collected, the more likely an accurate estimate of the PWV may be determined. However, the subject being measured may not have unlimited patience for numerous measurements if each application of counter pressure and corresponding measurement takes too long. Thus, the number of measurements used may be limited and set as a predetermined minimum. In this way, a processor may access the memory in which the pressure values and sensor measurements are stored to determine whether a sufficient number of data points have been collected. In response to determining that an additional measurement of the parameter(s) is/are needed (i.e., determination block 830="Yes"), the control unit may trigger a change in counter pressure in block 835, followed by the application of the changed counter pressure in block 810. In response to determining that an additional measurement of the parameter(s) is/are not needed (i.e., determination block 830="No"), the control unit may select a model (e.g., equation 7) in block 840 that may be used for estimating the unknown parameter(s) in block 850.

In block 840, the control unit may select a model from a set of models. The selection of a model may be based on best fit or other considerations. For example, fitting procedures may be used for the selection of the model, which may include a simple least squaring fitting or fitting including weights to values proportional to the corresponding applied external counter pressures. In addition, other techniques for fitting may be used such as least squares, weighted least squares (e.g., a fitting where the weighting is proportional to the counter pressure), iterative proportional fitting, matrix ranking, regression analysis, or differential or partial differential equation solutions. The model may be selected from a predetermined stress-strain relationship of the artery, a Bramwell-Hill equation, an exponential model, a bi-linear model, and/or others.

In block 850, the control unit may estimate one or more unknown parameters in the selected model, which establishes a relationship of the parameters to counter pressures. Using the model selected in block 840, the measured parameters and corresponding counter pressures may be used in the model to determine a value for the unknown parameters. Each data point may correspond to a different unknown parameter value, but a mean, median, or mode value may be used as the estimated value for the unknown parameter.

In block 860, the control unit may determine an estimated PWV based on the estimated unknown parameter(s). Once the estimated PWV is determined, an output may be provided by the control unit, such as for providing pressure reading using known conversion techniques, testing, diagnosis, or other uses. The output may indicate the estimated PWV and may be determined using no applied external counter pressure in the model used to determine the estimated PWV. The output may be recorded in a medical record or provided to the subject, a medical practitioner, a technician, or other entity. The control unit may repeat the operations of the method 800 following the determination of the estimated PWV in block 860, initiating the pressure device to, once again, apply a counter pressure in block 810. Optionally, the counter pressure may be changed before application in block 810.

The foregoing method descriptions and the process flow diagrams are provided merely as illustrative examples and are not intended to require or imply that the steps of various embodiments must be performed in the order presented. As will be appreciated by one of skill in the art the order of steps in the foregoing embodiments may be performed in more than one order. Words such as "thereafter," "then," "next," etc. are not intended to limit the order of the steps; these words are simply used to guide the reader through the description of the methods. Further, any reference to claim elements in the singular, for example, using the articles "a," "an," or "the" is not to be construed as limiting the element to the singular.

While the terms "first" and "second" are used herein, for example to describe parameters related to a pulse wave velocity or other elements, such identifiers are merely for convenience and are not meant to limit various embodiments to a particular order, sequence, type of network or carrier.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more embodiments, the functions described may be implemented in hardware, software, firmware, or any combination thereof. If implemented in software, the functions may be stored as one or more instructions or code on a non-transitory computer-readable medium or non-transitory processor-readable medium. The steps of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method of determining an estimated pulse wave velocity of an artery of a subject, comprising:
    applying a series of counter pressures at a set location on the subject over the artery with a pressure device, wherein each counter pressure of the series of counter pressures is different from one another, applied at the set location, and between zero and a diastolic pressure of the subject, and wherein the applying the series of counter pressures further includes:
        measuring, for each counter pressure of the series of counter pressures, a corresponding value of a first parameter related to pulse wave velocity when the respective counter pressure is applied;
        determining, with a control unit, after measuring the value of the first parameter corresponding to at least one counter pressure of the series of counter pressures, whether a sufficient number of values have been collected; and
        in response to determining a sufficient number of values have not been collected, measuring the value of the first parameter corresponding to an additional counter pressure of the series of counter pressures;
    for each model of a predetermined set of models that establishes a relationship of the first parameter to each counter pressure of the series of counter pressures, performing a fitting procedure to determine a fit of the respective model to the measured values of the first parameter, wherein performing the fitting procedure comprises weighting a higher counter pressure more heavily than a lower counter pressure among the series of counter pressures;
    selecting a best-fit model from the predetermined set of models based on a result of the fitting procedure performed for each model of the predetermined set of models;
    estimating a second parameter using the selected model; and
    determining the estimated pulse wave velocity based on the second parameter estimated using the selected model.

2. The method of claim 1, wherein the series of counter pressures each apply a pressure force in such a way that the pressure force is applied perpendicular to a longitudinal direction of a limb containing the artery.

3. The method of claim 1, wherein the series of counter pressures are each applied by a tightening band worn by the subject at the set location.

4. The method of claim 3, wherein measuring, for each counter pressure of the series of counter pressures, the corresponding value of the first parameter includes using two sensors disposed between the tightening band and a portion of skin of the subject.

5. The method of claim 3, wherein measuring, for each counter pressure of the series of counter pressures, the corresponding value of the first parameter includes using two sensors disposed on a portion of skin of the subject and outside opposed ends of the tightening band.

6. The method of claim 3, wherein measuring the first value includes using an ultrasound sensor embedded inside the tightening band.

7. The method of claim 1, wherein measuring, for each counter pressure of the series of counter pressures, the corresponding value of the first parameter includes measuring across a span of less than 20 cm at the set location, wherein the series of counter pressures are each applied along the span.

8. The method of claim 1, wherein measuring, for each counter pressure of the series of counter pressures, the corresponding value of the first parameter includes using two sensors separated by a span along the artery to measure a transit time of a pulse between the two sensors.

9. The method of claim 1, wherein measuring, for each counter pressure of the series of counter pressures, the corresponding value of the first parameter includes detecting a distension of the artery over time.

10. The method of claim 1, wherein measuring, for each counter pressure of the series of counter pressures, the corresponding value of the first parameter includes measuring a first set of parameters.

11. The method of claim 1, wherein, for each counter pressure of the series of counter pressures, the corresponding value of the first parameter is measured using a technology selected from the group consisting of tonometry, ultrasound, nuclear magnetic resonance, a propagation property of electro-magnetic waves, an optical measurement, and bioelectrical impedance.

12. The method of claim 1, wherein the second parameter estimated using the selected model includes a second set of parameters.

13. The method of claim 1, wherein the predetermined set of models is selected from the group consisting of at least one of a predetermined stress-strain relationship of the artery, a Bramwell-Hill equation, an exponential model, and a bi-linear model.

14. A device for determining an estimated pulse wave velocity of an artery of a subject, comprising:
  a pressure device configured to apply a series of counter pressures at a set location on the subject over the artery, wherein each counter pressure of the series of counter pressures is different from one another, applied at the set location, and between zero and a diastolic pressure of the subject;
  a sensor configured to measure, for each counter pressure of the series of counter pressures, a corresponding value of a first parameter related to pulse wave velocity when the respective counter pressure is applied; and
  a processor coupled to the pressure device and the sensor, the processor configured with processor-executable instruction to perform operations comprising:
    determining, after the sensor measures the value of the first parameter corresponding to at least one counter pressure of the series of counter pressures, whether a sufficient number of values have been collected;
    in response to determining a sufficient number of values have not been collected, causing the sensor to measure the value of the first parameter corresponding to an additional counter pressure of the series of counter pressures;
    for each model of a predetermined set of models that establishes a relationship of the first parameter measured to each counter pressure of the series of counter pressures, performing a fitting procedure to determine a fit of the respective model to the measured values of the first parameter, wherein performing the fitting procedure comprises weighting a higher counter pressure more heavily than a lower counter pressure among the series of counter pressures;
    selecting a best-fit model from a predetermined set of models based on a result of the fitting procedure performed for each model of the predetermined set of models;
    estimating a second parameter using the selected model; and
    determining the estimated pulse wave velocity based on the second parameter estimated using the selected model.

15. The device of claim 14, wherein the series of counter pressures each apply a pressure force perpendicular to a longitudinal direction of a limb containing the artery.

16. The device of claim 14, wherein the pressure device includes a tightening band worn by the subject at the set location.

17. The device of claim 16, wherein the sensor includes two sensors disposed between the tightening band and a portion of skin of the subject.

18. The device of claim 16, wherein the sensor includes two sensors disposed on a portion of skin of the subject and outside opposed ends of the tightening band.

19. The device of claim 16, wherein the sensor includes an ultrasound sensor embedded inside the tightening band.

20. The device of claim 14, wherein the sensor is configured to measure the first parameter across a span of less than 20 cm at the set location, wherein the series of counter pressures are each applied along the span.

21. The device of claim 14, wherein the sensor includes two sensors separated by a span along the artery to measure a transit time of a pulse between the two sensors.

22. The device of claim 14, wherein the sensor is configured to detect a distension of the artery over time.

23. The device of claim 14, wherein the sensor is configured to measure a first set of parameters.

24. The device of claim 14, wherein the sensor includes a technology selected from the group consisting of tonometry, ultrasound, nuclear magnetic resonance, a propagation property of electro-magnetic waves, an optical measurement, and bioelectrical impedance.

25. The device of claim 14, wherein the processor is configured such that the second parameters includes a second set of parameters.

26. The device of claim 14, wherein the processor is configured with processor-executable instructions to perform operations such that the predetermined set of models is selected from the group consisting of at least one of a predetermined stress-strain relationship of the artery, a Bramwell-Hill equation, an exponential model, and a bi-linear model.

27. A device for determining an estimated pulse wave velocity of an artery of a subject, comprising:
  means for applying a series of counter pressures at a set location on the subject over the artery with a pressure device, wherein each counter pressure of the series of counter pressures is different from one another, applied at the set location, and between zero and a diastolic pressure of the subject , and wherein the applying the series of counter pressures further includes:
    means for measuring, for each counter pressure of the series of counter pressures, a corresponding value of a first parameter related to pulse wave velocity when the respective counter pressure is applied;
    means for determining, after measuring the value of the first parameter corresponding to at least one counter pressure of the series of counter pressures, whether a sufficient number of values have been collected; and means for measuring, in response to determining a sufficient number of values have not been collected, the value of the first parameter corresponding to an additional counter pressure of the series of counter pressures;

means for performing a fitting procedure, for each model of a predetermined set of models that establishes a relationship of the first parameter to each counter pressure of the series of counter pressures, to determine a fit of the respective model to the measured values of the first parameter, wherein the fitting procedure comprises weighting a higher counter pressure more heavily than a lower counter pressure among the series of counter pressures;

means for selecting a best-fit model from the predetermined set of models based on a result of the fitting procedure performed for each model of the predetermined set of models;

means for estimating a second parameter using the selected model; and means for determining the estimated pulse wave velocity based on the second parameter estimated using the selected model.

28. The device of claim 27, wherein means for applying the series of counter pressures comprises means for applying each counter pressure so that a pressure force is applied perpendicular to a longitudinal direction of a limb containing the artery.

29. The device of claim 27, wherein means for applying the series of counter pressures include means for tightening a tightening band worn by the subject at the set location.

30. The device of claim 29, wherein means for measuring, for each counter pressure of the series of counter pressures, the corresponding value of the first parameter includes means for measuring elements of the first parameter disposed between the tightening band and a portion of skin of the subject.

31. The device of claim 29, wherein means for measuring, for each counter pressure of the series of counter pressures, the corresponding value of the first parameter includes means for measuring elements of the first parameter disposed on a portion of skin of the subject and outside opposed ends of the tightening band.

32. The device of claim 29, wherein means for measuring the first parameter includes means for measuring ultrasound embedded inside the tightening band.

33. The device of claim 27, wherein means for measuring, for each counter pressure of the series of counter pressures, the corresponding value of the first parameter comprises means for measuring the first parameter across a span of less than 20 cm at the set location, wherein with each of the series of counter pressures applied along the span.

34. The device of claim 27, wherein means for measuring, for each counter pressure of the series of counter pressures, the corresponding value of the first parameter includes means for measuring elements of the first parameter separated by a span along the artery to measure a transit time of a pulse through the span.

35. The device of claim 27, wherein means for measuring, for each counter pressure of the series of counter pressures, the corresponding value of the first parameter includes means for detecting a distension of the artery over time.

36. The device of claim 27, wherein means for measuring, for each counter pressure of the series of counter pressures, the corresponding value of the first parameter includes means for measuring a first set of parameters.

37. The device of claim 27, wherein means for measuring, for each counter pressure of the series of counter pressures, the corresponding value of the first parameter includes a technology selected from the group consisting of tonometry, ultrasound, nuclear magnetic resonance, a propagation property of electro-magnetic waves, an optical measurement, and bioelectrical impedance.

38. The device of claim 27, wherein means for estimating the second parameter includes means for estimating a second set of parameters.

39. The device of claim 27, wherein the predetermined set of models is selected from the group consisting of at least one of a predetermined stress-strain relationship of the artery, a Bramwell-Hill equation, an exponential model, and a bi-linear model.

40. A non-transitory processor-readable storage medium having stored thereon processor-executable instructions configured to cause a processor to perform operations for determining an estimated pulse wave velocity of an artery of a subject, the operations comprising:

applying a series of counter pressures at a set location on the subject over the artery with a pressure device, wherein each counter pressure of the series of counter pressures is different from one another, applied at the set location, and between zero and a diastolic pressure of the subject, and wherein the applying the series of counter pressures further includes:

measuring, for each counter pressure of the series of counter pressures, a corresponding value of a first parameter related to pulse wave velocity when each of the series of counter pressures is applied;

determining, after measuring the value of the first parameter corresponding to at least one counter pressure of the series of counter pressures, whether a sufficient number of values have been collected; and in response to determining a sufficient number of values have not been collected, measuring the value of the first parameter corresponding to an additional counter pressure of the series of counter pressures;

for each model of a predetermined set of models that establishes a relationship of the first parameter to each counter pressure of the series of counter pressures, performing a fitting procedure to determine a fit of the respective model to the measured values of the first parameter, wherein performing the fitting procedure comprises weighting a higher counter pressure more heavily than a lower counter pressure among the series of counter pressures;

selecting a best-fit model from the predetermined set of models based on a result of the fitting procedure performed for each model of the predetermined set of models;

estimating a second parameter using the selected model; and determining the estimated pulse wave velocity based on the second parameter estimated using the selected model.

41. The non-transitory processor-readable storage medium of claim 40, wherein the stored processor-executable instructions are configured to cause the processor to perform operations such that the series of counter pressures each apply a pressure force perpendicular to a longitudinal direction of a limb containing the artery.

42. The non-transitory processor-readable storage medium of claim 40, wherein the series of counter pressures are each applied by a tightening band worn by the subject at the set location.

43. The non-transitory processor-readable storage medium of claim 42, wherein the stored processor-executable instructions are configured to cause the processor to perform operations such that measuring, for each counter pressure of the series of counter pressures, the corresponding value of the first parameter includes using two sensors disposed between the tightening band and a portion of skin of the subject.

44. The non-transitory processor-readable storage medium of claim 42, wherein the stored processor-executable instructions are configured to cause the processor to perform operations such that measuring, for each counter pressure of the series of counter pressures, the corresponding value of the first parameter includes using two sensors disposed on a portion of skin of the subject and outside opposed ends of the tightening band.

45. The non-transitory processor-readable storage medium of claim 42, wherein the stored processor-executable instructions are configured to cause the processor to perform operations such that measuring, for each counter pressure of the series of counter pressures, the corresponding value of the first parameter includes using an ultrasound sensor embedded inside the tightening band.

46. The non-transitory processor-readable storage medium of claim 40, wherein the stored processor-executable instructions are configured to cause the processor to perform operations such that measuring, for each counter pressure of the series of counter pressures, the corresponding value of the first parameter includes measuring across a span of less than 20 cm at the set location, wherein the series of counter pressures are each applied along the span.

47. The non-transitory processor-readable storage medium of claim 40, wherein the stored processor-executable instructions are configured to cause the processor to perform operations such that measuring, for each counter pressure of the series of counter pressures, the corresponding value of the first parameter includes using two sensors separated by a span along the artery to measure a transit time of a pulse between the two sensors.

48. The non-transitory processor-readable storage medium of claim 40, wherein the stored processor-executable instructions are configured to cause the processor to perform operations such that measuring, for each counter pressure of the series of counter pressures, the corresponding value of the first parameter includes detecting a distension of the artery over time.

49. The non-transitory processor-readable storage medium of claim 40, wherein the stored processor-executable instructions are configured to cause the processor to perform operations such that measuring, for each counter pressure of the series of counter pressures, the corresponding value of the first parameter includes measuring a first set of parameters.

50. The non-transitory processor-readable storage medium of claim 40, wherein the stored processor-executable instructions are configured to cause the processor to perform operations such that, for each counter pressure of the series of counter pressures, the corresponding value of the first parameter is measured using a technology selected from the group consisting of tonometry, ultrasound, nuclear magnetic resonance, a propagation property of electro-magnetic waves, an optical measurement, and bioelectrical impedance.

51. The non-transitory processor-readable storage medium of claim 40, wherein the stored processor-executable instructions are configured to cause the processor to perform operations such that the second parameter estimated using the selected model includes a second set of parameters.

52. The non-transitory processor-readable storage medium of claim 40, wherein the stored processor-executable instructions are configured to cause the processor to perform operations such that the predetermined set of models is selected from the group consisting of at least one of a predetermined stress-strain relationship of the artery, a Bramwell-Hill equation, an exponential model, and a bi-linear model.

* * * * *